(12) United States Patent
Hassell et al.

(10) Patent No.: US 6,202,241 B1
(45) Date of Patent: Mar. 20, 2001

(54) BRUSHHEAD FOR USE IN AN ACOUSTIC TOOTHBRUSH

(75) Inventors: Thomas Hassell, Kirkland; Stephen M. Meginness, III; James C. McInnes, both of Seattle, all of WA (US)

(73) Assignee: Optiva Corporation, Snoqualmie, WA (US)

( * ) Notice: Subject to any disclaimer, the term of this patent is extended or adjusted under 35 U.S.C. 154(b) by 0 days.

(21) Appl. No.: 09/150,877

(22) Filed: Sep. 10, 1998

(51) Int. Cl.$^7$ .............................. A46B 9/04; A61C 17/22
(52) U.S. Cl. .................. 15/22.1; 15/167.1; 15/DIG. 5; D4/101; D4/104
(58) Field of Search ................. 15/22.1, 167.1, 15/DIG. 5; D4/101, 104

(56) References Cited

U.S. PATENT DOCUMENTS

| | | | |
|---|---|---|---|
| 335,345 | * | 2/1886 | Estabrook ........................... 15/167.1 |
| D. 397,251 | * | 8/1998 | Eguchi et al. ........................ D4/101 |
| 1,059,426 | * | 4/1913 | Barnes ................................ 15/167.1 |
| 1,657,450 | * | 1/1928 | Barnes ................................ 15/167.1 |
| 1,943,225 | * | 1/1934 | McIntyre ............................. 15/167.1 |
| 2,097,987 | * | 11/1937 | Phillips ............................... 15/167.1 |
| 2,209,173 | * | 7/1940 | Russell ............................... 15/167.1 |
| 2,978,724 | * | 4/1961 | Gracian .............................. 15/167.1 |
| 3,188,673 | * | 6/1965 | Newman ............................. 15/167.1 |
| 3,840,932 | | 10/1974 | Balamuth et al. .................. 15/167.1 |
| 3,934,298 | * | 1/1976 | Kim .................................... 15/167.1 |
| 4,033,008 | * | 7/1977 | Warren et al. ...................... 15/167.1 |
| 4,268,933 | * | 5/1981 | Papas ................................. 15/167.1 |
| 4,356,585 | * | 11/1982 | Protell et al. ................... 15/167.1 X |
| 4,403,623 | * | 9/1983 | Mark .................................. 15/167.1 |
| 4,672,706 | * | 6/1987 | Hill .................................... 15/167.1 |
| 4,724,569 | * | 2/1988 | Eguchi et al. ..................... 15/DIG. 5 |
| 4,776,055 | * | 10/1988 | Nelson ............................... 15/167.1 |
| 5,305,492 | | 4/1994 | Giuliani et al. .................... 15/176.1 |
| 5,378,153 | | 1/1995 | Giuliani et al. .................... 433/216 |
| 5,459,898 | * | 10/1995 | Bacolot ......................... 15/167.1 X |
| 5,511,275 | | 4/1996 | Volpenhein et al. ............... 15/167.1 |
| 5,655,249 | * | 8/1997 | Li ....................................... 15/167.1 |
| 5,735,011 | | 4/1998 | Asher ................................. 15/167.1 |
| 5,896,614 | | 4/1999 | Flewitt .............................. 15/167.1 |

FOREIGN PATENT DOCUMENTS

| | | | |
|---|---|---|---|
| 274680 | * | 7/1988 | (EP) ................................. 15/167.1 |
| 596633 | * | 5/1994 | (EP) ................................. 15/167.1 |
| 695325 | * | 12/1930 | (FR) ................................. 15/167.1 |

OTHER PUBLICATIONS

*Periodontal Diseases,* 2nd Ed., Lea & Febriger 1990, pp 356–358.
*Periodontal Therapy,* 5th Ed., C. V. Mosby Company 1974, pp 429–432.
Jordan V toothbrush (photography of packaging showing brush configuration).
Zahoransky toothbrush (pictures of actual toothbrush).
Butler toothbrush (photocopy of ad showing toothbrush configuration).

* cited by examiner

*Primary Examiner*—Mark Spisich
(74) *Attorney, Agent, or Firm*—Jensen & Puntigam, P.S.

(57) ABSTRACT

A brushhead for an acoustic powered toothbrush having a particular bristle configuration which includes a plurality of bristle portions arranged in four columns and eight rows, wherein the distal end two adjacent rows and the proximal end two adjacent rows both have longer bristles than the remaining bristle portions except for an intermediate row of bristle portions which are slightly longer than the longer bristle portions. The distal, intermediate and proximal bristle portions all have pointed bristle portion tips.

11 Claims, 2 Drawing Sheets

BRUSHHEAD FOR USE IN AN ACOUSTIC TOOTHBRUSH

DESCRIPTION

1. Technical Field

This invention relates generally to acoustic (power) toothbrushes, and more specifically concerns a particular brushhead configuration for use with such toothbrushes.

2. Background of the Invention

Conventional toothbrush brushhead configurations tend to focus on the mechanical cleaning of the large, easily accessible buccal (exterior) and lingual (interior, adjacent the tongue) surfaces of the teeth. However, other areas of the dental region, including those teeth at the very rear of the mouth, and the interdental areas between the teeth, are more difficult to clean and are therefore often the site of dental disease. While there are some toothbrush brushhead configurations which are indicated to be effective for interdental regions, little improvement is typically experienced with such brushhead configurations. Hence, one significant issue with existing toothbrush configurations is the lack of effectiveness in difficult-to-reach areas. In some cases, interdental regions are reached beyond the tips of the bristles by the action of the toothbrush itself, such as with the toothbrush shown in U.S. Pat. No. 5,378,153, owned by the assignee of the present invention. However, even with such toothbrushes, it would be desirable to have a brushhead design which could give better coverage and/or penetration for the difficult-to-reach areas.

In addition to the problem of difficult-to-reach areas, many brushhead designs which are quite effective in removing plaque from teeth produce damage to the surrounding oral tissues which the bristles contact in the oral cavity. This is particularly true for power toothbrushes. Accordingly, it would be desirable for a brushhead to have a design which results in an enhanced cleansing effect in the difficult-to-reach areas, including the rear teeth surfaces and the interdental surfaces, but which also minimizes abrasion of the surrounding oral tissue.

DISCLOSURE OF THE INVENTION

Accordingly, the present invention is a brushhead for use with a vibrating toothbrush which uses fluid to produce an acoustic cleaning effect on the teeth, wherein the vibrating toothbrush has an operating frequency in the range of 150 to 400 Hz, and wherein the brushhead comprises: a brushhead base member; and a plurality of bristle portions mounted in the brushhead base member and arranged to define a bristle portion group, wherein at least some of the bristle portions are shorter than the remaining longer bristle portions, wherein the longer bristle portions are located at opposing ends of the bristle portion group, and wherein the longer bristle portions have an angled tip within the range of 56° to 72° to improve dental penetration by the bristles.

In another aspect of the brushhead, the plurality of bristle portions are arranged into rows and columns to define a bristle portion group in a brushhead base member which has an outline of approximately 1.85 inches long by approximately 0.3 inches wide, wherein the bristle portions include four spaced columns, the columns having centerlines which are separated by a distance of approximately 0.07 inches and wherein the four columns of bristle portions relative to the brushhead base member have a size which results in a decrease in the abrasive effect on the tissue surrounding the teeth relative to a brushhead having fewer columns and bristle portions on a similar base member, without affecting negatively the cleaning action of the brushhead portions.

In yet another aspect of such a brushhead having a brushhead base member, a plurality of bristle portions are arranged in columns and rows to define a bristle portion group wherein some of the bristle portions are shorter than the remaining longer bristle portions, wherein the longer bristle portions are located at distal and proximal ends of the bristle portion group and at one intermediate position between said two ends, wherein the brushhead includes two adjacent rows of shorter bristle portions between the distal end bristle portions and the intermediate position bristle portion, and at least one row of shorter bristle portions between the proximal end bristle portions and the intermediate position bristle portion, wherein the space between the distal end bristle portions and the intermediate position bristle portion accommodates posterior teeth, while the space between the intermediate position bristle portion and the proximal end bristle portions accommodates anterior teeth, so as to provide better coverage for the teeth.

In still another aspect of such a brushhead, a plurality of bristle portions are mounted in the brushhead base member defining a bristle portion group, the bristle portions including a first set of shorter bristle portions, a second set of longer bristle portions and a third set of longest bristle portions which are slightly longer than the second set of longer bristle portions, wherein the longer bristle portions are located at opposing longitudinal ends of the bristle portion group and wherein the longest bristle portions are located intermediate of the opposing longitudinal ends of the bristle portion group, wherein the shorter bristle portions are located between the longer bristle portions and the longest bristle portions, and when the longest bristle portions provide increased interdental penetration of the teeth during use, resulting in improvement of plaque removal.

BEST MODE FOR CARRYING OUT THE INVENTION

Figure 1:
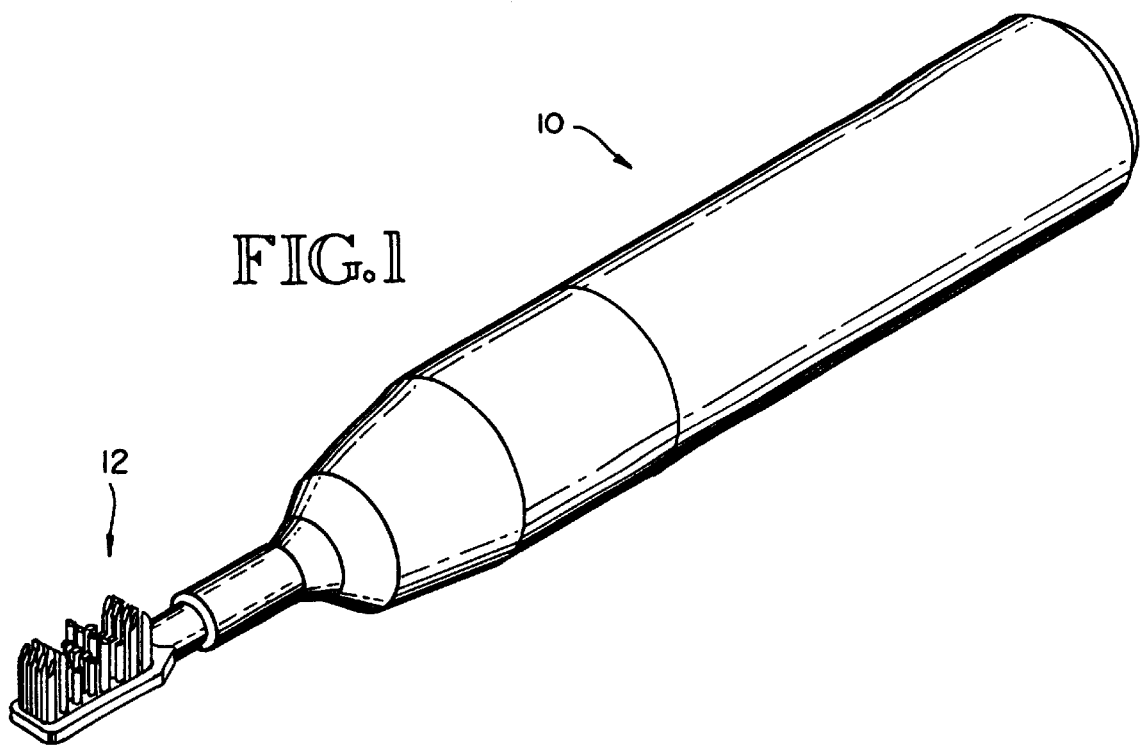
FIG. 1 is a perspective view of a power toothbrush with the brushhead configuration of the present invention.

FIG. 1 shows a power toothbrush generally at 10. The brushhead of the present invention, shown at 12, is positioned at the distal end of a lever arm portion of the power toothbrush. Toothbrush 10 operates with a brushhead frequency and amplitude which disrupts bacteria and removes plaque from the teeth of the user, including in the interdental regions, i.e. the regions between the teeth, and/or the subgingival regions between the gum and the teeth, as well as the hard-to-reach surfaces at the very rear of the mouth.

With the toothbrush shown, a fluid environment is maintained in the mouth so that the acoustic pressure created by movement of the brushhead within the mouth is coupled to the fluid in the interdental and subgingival regions of the teeth, while at the same time the sweeping action of the bristles mechanically removes plaque from the exposed areas of the teeth. While the brushhead 12 of the present invention is shown in the context of a particular power toothbrush, it should be understood that the brushhead could be used with a variety of power toothbrushes, particularly those within a certain frequency range, i.e. 150–400 Hz. A more precise operating frequency for the toothbrush is approximately 260 Hz.

Figure 2:
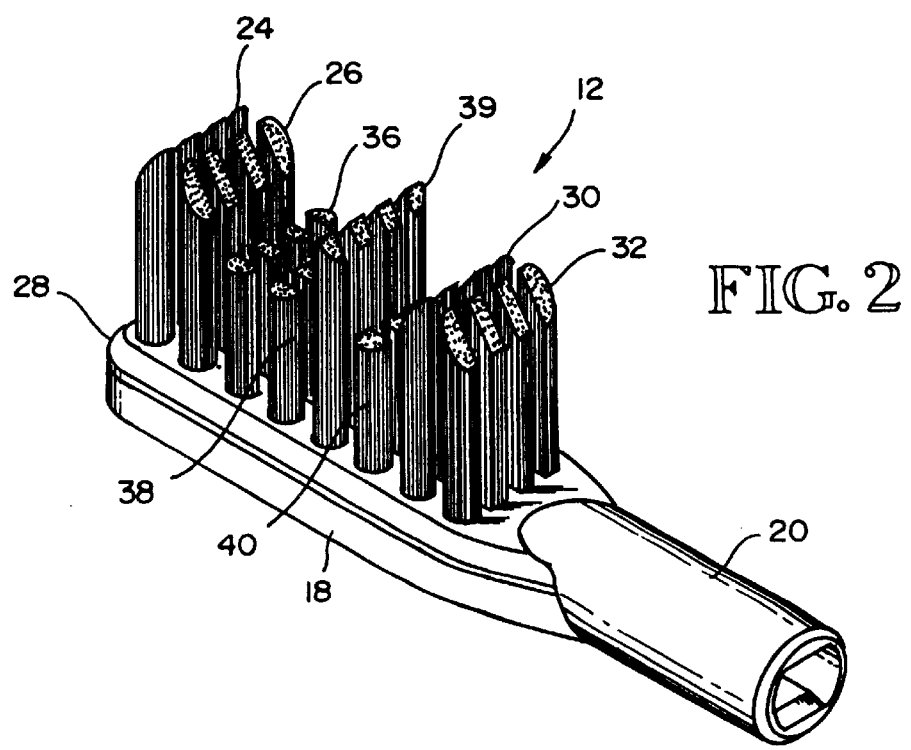
FIG. 2 is a perspective view of the brushhead shown in FIG. 1.
Figure 3:
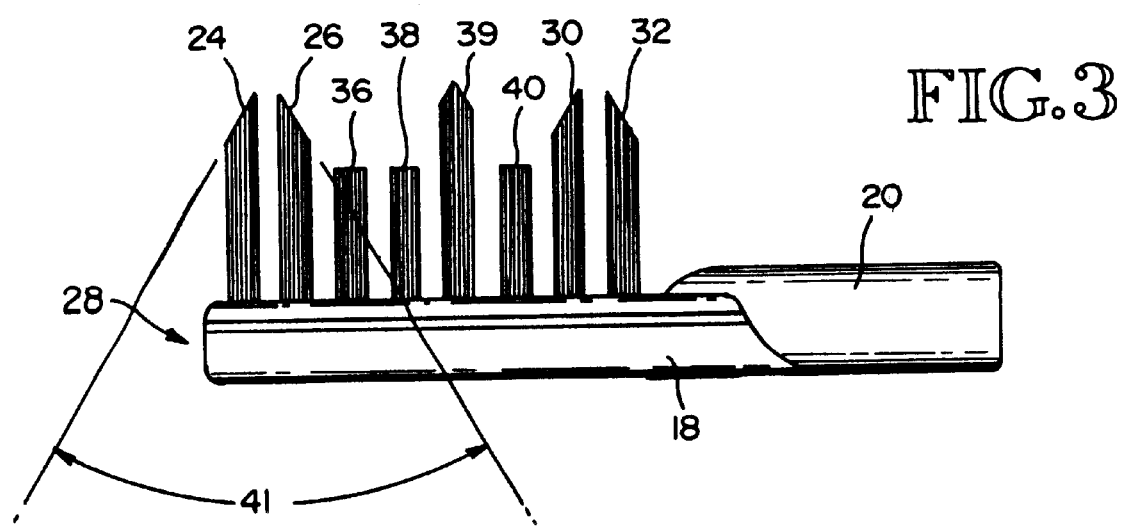
FIG. 3 is a side elevational view of the brushhead of FIG. 2.
Figure 4:
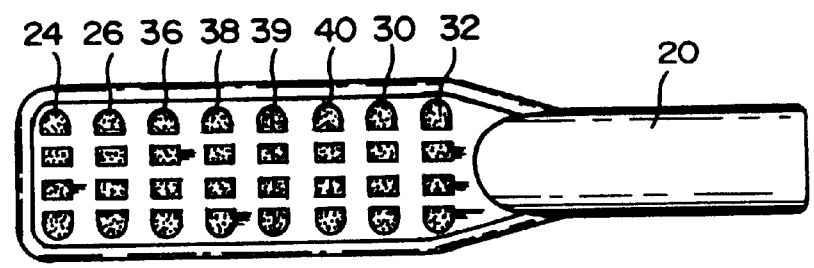
FIG. 4 is a top view of the brushhead of FIG. 2.

FIGS. 2, 3 and 4 show the brushhead arrangement of the present invention. Brushhead 12 includes a flat base portion 18. In the embodiment shown, base portion 18 is approximately 1.85 inches long by approximately 0.35 inches wide, and approximately 0.15 inches thick, with all dimensions being ±10%. At the proximal end of brushhead 12 is a connecting portion 20 which is hollow so it can receive a free end of a lever arm portion of the toothbrush.

The bristles on the brushhead are arranged in a pattern of four columns and eight rows of bristle groups in the embodiment shown with the columns extending longitudinally of the brushhead and the rows extending laterally thereof. In the embodiment shown, each bristle group comprises approximately 38 ±4 bristle strands, with the bristle strands in the embodiment shown being made from nylon, in one embodiment Dupont Tynex.

Using four columns instead of the conventional three results in a significant increase in bristle density. This increase in density, by increasing the total number of bristle strands, also known as tufts, in the same base area, produces both an improvement in the effect of the brushing and also, surprisingly, reduces abrasion; there is hence a reduction in harm to the oral tissue regions. Thus, the particular density of the individual bristle groups of the toothbrush are a significant aspect of the present invention. In the embodiment shown, the centerlines of the four columns are separated by approximately 0.07 inches and the centerlines of the rows are separated by approximately 0.1 inches.

In the embodiment shown, the brushhead has a particular arrangement of bristle strand or tuft lengths. Adjacent rows 24 and 26 at the distal end 28 of the brushhead are long bristles, having a total length from the base portion 18 of the brushhead of approximately 0.41 inches ±0.01 inches. The two adjacent rows 30 and 32 at the proximal end of the brushhead are also long bristles, also having a maximum length of 0.41±0.01 inches.

Rows 36 and 38, which are two adjacent, successive rows of bristle portions inboard of distal rows 24 and 26 are both relatively short, approximately 0.26±0.01 inches long from base portion 18.

The next row of bristle portions inboard of row 38 is a single row 39 having a longest bristle strand length of 0.435 inches ±0.02 inches. This row of bristle portions has bristle strands with a slightly smaller diameter than the bristle strands in the other bristle portions, in particular a 0.005 inch diameter as opposed to a 0.006 inch diameter. The combination of a single row with the bristle strands therein (1) being slightly longer than the long bristle strands of rows 24 and 26, (2) located approximately in the middle of the brushhead and (3) having a slightly smaller diameter than the other bristle strands, provides an increase in penetration of the bristles into, and a better fit for, the interdental region. Further, the extra long, small diameter bristles are less harmful to the gum tissue than conventional bristles.

The next row 40 of bristle portions is another short bristle length row, also approximately 0.26±0.01 inches long, similar to rows 36 and 38. Row 40 is located between the longest bristle length row 39 and the two rear proximal end rows 30 and 32. The total spacing between the distal long rows 24 and 26 and the central longest row 39 is designed to accommodate the posterior teeth, i.e. those teeth toward the rear of the mouth, while the total space between the longest row 39 and the proximal end long row 30 is designed to accommodate the anterior teeth, i.e. the teeth toward the front of the mouth. The short rows 36 and 38 brush against the sides of the posterior (molar) teeth, while the short row 40 brushes against the sides of the anterior teeth.

Hence, the overall brushhead configuration shown in FIGS. 2–4 tends to more accurately accommodate the actual arrangement and various sizes of the teeth in the mouth, so as to provide better and more uniform bristle coverage for the teeth and hence better cleansing action. The bristle portions of the embodiment shown as a unit thus better fits the variety of teeth sizes actually present in the human mouth.

The short bristle rows 36, 38 and 40 all have flat tops, although each individual bristle strand is rounded. On the other hand, the long distal end rows 24 and 26, the long proximal end rows 30 and 32, and the intermediate longest row 39 all have angled bristle portions, as shown in FIG. 2 and 3, even though each individual bristle strand is rounded, as indicated above. The distal end long row pair and the proximal end long row pair angle to a point, while longest row 39 is itself configured to a point. The bristle angle 41 (shown in FIG. 3) is within the range of 56° to 72°. It has been discovered that this range of angle is actually quite significant in improving the effects of the brush. The range of angle improves plaque removal on all the teeth, and especially improves interdental cleaning.

Hence, a new brushhead configuration for a power toothbrush has been described which incorporates several specific improvements, resulting in improved performance and cleansing, while decreasing abrasion.

Although a preferred embodiment of the invention has been disclosed herein for illustration, it should be understood that various changes, modifications and substitutions may be incorporated in such embodiment without departing from the spirit of the invention, which is defined by the claims as follows.

What is claimed is:

1. A brushhead for use with a vibrating toothbrush which uses fluid to produce an acoustic cleaning effect on the teeth, the brushhead comprising:

a brushhead base member; and a plurality of bristle portions mounted in the brushhead base member and arranged to define a bristle portion group, wherein at least some of the bristle portions are shorter than the remaining longer bristle portions, wherein the longer bristle portions are located at opposing ends of the bristle portion group, and wherein the longer bristle portions at both ends of the bristle portion group have and angled tip within the range of 56° to 72° for improved interdental penetration by the bristles, the bristle portion group further including a section of bristle portion between the longer bristle portions which are longer than the longer bristle portions.

2. An article of claim 1, wherein the angled tip is approximately 60°.

3. An article of claim 1, wherein the bristle portion group has eight rows and four columns and wherein two adjacent distal end rows and two adjacent proximal end rows have said longer bristles.

4. An article of claim 1, wherein the tip of each bristle in the bristle portions is rounded.

5. A brushhead for use with a vibrating toothbrush which uses fluid to produce an acoustic cleaning effect on teeth, the brushhead comprising:

a brushhead base member; and a plurality of bristle portions arranged in columns and rows to define a bristle portion group, wherein some of the bristle portions are shorter than the remaining longer bristle portions, wherein the longer bristle portions are located at distal and proximal ends of the bristle portion group and one intermediate position between said two ends, wherein the brushhead includes two adjacent rows of shorter bristle portions between the distal end bristle portions and the intermediate position bristle portion, and one row of shorter bristle portions between the proximal end bristle portions and the intermediate position bristle portion, wherein the space between the distal end bristle portions and the intermediate position bristle portion accommodates posterior teeth, while the space between the intermediate position bristle portion and the proximal end bristle portions accommodates anterior teeth, so as to provide better coverage for the teeth during brushing.

6. An article of claim 5, wherein the longer bristle portions and the intermediate position bristle portion all have a pointed tip configuration.

7. A brushhead for use with a vibrating toothbrush which uses fluid to produce an acoustic cleaning effect on teeth, the brushhead comprising:

a brushhead base member; and a plurality of bristle portions mounted in the brushhead base member, defining a bristle portion group, the bristle portions including a first set of shorter bristle portions, a second set of longer bristle portions, and a third set of longest bristle portions which are slightly longer than the second set of longer bristle portions, wherein the longer bristle portions are located at opposing longitudinal ends of the bristle portion group and wherein the longest bristle portions are located intermediate of the opposing longitudinal ends of the bristle portion group, wherein the shorter bristle portions are located between the longer bristle portions and the longest bristle portions, and wherein the longest bristle portions provide increased interdental penetration of the teeth during use, resulting in improvement of plaque removal.

8. An article of claim 7 wherein the longest bristle portions comprise bristle strands which are thinner than the bristle strands comprising the shorter and longer bristle portions.

9. An article of claim 7, wherein the longer bristle portions comprise two adjacent rows at the distal and proximal ends of the base member and the longest bristle portions comprise one row located intermediate of the rows of the longer bristle portions.

10. An article of claim 7, wherein the bristle tips of the longer and longest bristle portions all have a pointed tip configuration.

11. A brushhead for use with a vibrating toothbrush which uses fluid to produce an acoustic cleaning effect on the teeth, the brushhead comprising:

a brushhead base member; and a plurality of bristle portions mounted in the brushhead base member and arranged to define a bristle portion group, wherein at least some of the bristle portions are shorter than the remaining longer bristle portions, wherein the longer bristle portions are located at opposing ends of the bristle portion group, and wherein the longer bristle portions at both ends of the bristle portion group have an angle tip within the range of 56° to 72° degrees for improved interdental penetration by the bristles, wherein the bristle portion group has eight rows and four columns and wherein two adjacent distal end rows and two adjacent proximal end rows have said longer bristles.

* * * * *